United States Patent [19]
Chiodi

[11] Patent Number: 5,229,364
[45] Date of Patent: Jul. 20, 1993

[54] POLYPEPTIDES DERIVED FROM THE HUMAN IMMUNODEFICIENCY VIRUS ENDONUCLEASE PROTEIN

[76] Inventor: Francesca Chiodi, Hagatan 12, S11348 Stockholm, Sweden

[21] Appl. No.: 670,296

[22] Filed: Mar. 15, 1991

[51] Int. Cl.$^5$ .................... A61K 37/00; C07K 5/00
[52] U.S. Cl. ........................ 514/12; 514/13; 514/14; 514/15; 530/324; 530/325; 530/326; 530/327; 530/328; 530/806
[58] Field of Search ............ 514/12, 13, 15, 14; 530/326, 328, 806, 324, 325, 327

[56] References Cited
PUBLICATIONS

Grandgenett et al., (1978) *Virology*, 89:119–132.
Lillehoj et al., (1988) *J. Virol.*, 62:8, 3053–3058.
Steimer et al., (1986) *J. Virol.*, 58(1):9–16.
Allan et al., (1987) *Blood*, 69(1):331–333.
Houghten et al., (1985) *Proc. Natl. Acad. Sci. USA*, 82:5131–5135.
Meyers et al., (1990) *Human Retroviruses and AIDS 1990*, pp. II-14-II-21.
Center for Disease Control, (1986) *JAMA* Jul. 4, 256(1):20–25.
Wang et al., (1986) *Proc. Natl. Acad. Sci. USA*, 83:6159–6163.
Palker et al., (1987) *Proc. Natl. Acad. Sci. USA*, 84:2479–2483.
Palker et al., (1988) *Proc. Natl. Acad. Sci. USA*, 85:1932–1936.
Norrby et al., (1987) *Nature*, 329:248–250.
Norrby et al., *AIDS Res. Human Retroviruses*, (1991) 279–284.
Broliden et al., *J. Acquired Immune Deficiency Syndrome*, (1991) 4:952–958.
Goudsmit et al., (1989) *J. AIDS*, 2:297–302.
Kyte et al., (1982) *J. Mol. Biol.*, 157:105–132.
Chou et al., (1978) *Adv. Enzymol.*, 47:45–148.
Kopchick et al., (1981) *J. Virol.*, 37:274–283.
Panet et al., (1975) *Proc. Natl. Acad. Sci.*, 72:2535–2539.
Panganiban et al., (1984) *Proc. Natl. Acad. Sci. USA*, 81:7885–7889.
Donehower et al., (1984) *Proc. Natl. Acad. Sci. USA*, 81:6461–6465.
Tam et al., (1983) *J. Am. Chem. Soc.*, 105:6442–6455.
Houghten et al., (1986) *Int. J. Pept. Protein Res.*, 27:673–678.

*Primary Examiner*—Merrell C. Cashion, Jr.
*Assistant Examiner*—Bennett Celsa
*Attorney, Agent, or Firm*—Dressler, Goldsmith, Shore, Sutker & Milnamow, Ltd.

[57] ABSTRACT

A polypeptide of the formula (SEQ ID NO 24): X-Glu-Thr-Gly-Gln-Glu-Thr-Ala-Tyr-Phe-Ile-Leu-Lys-Leu-Ala-Gly-Arg-Trp-Pro-Val-Lys-Z wherein X is a chain of from 1 to 20 amino acid residues or an amino-terminal group and Z is a chain of from 1 to 20 amino acid residues or a carboxy-terminal group. The polypeptide immunologically mimics HIV endonuclease (p 31).

5 Claims, 2 Drawing Sheets

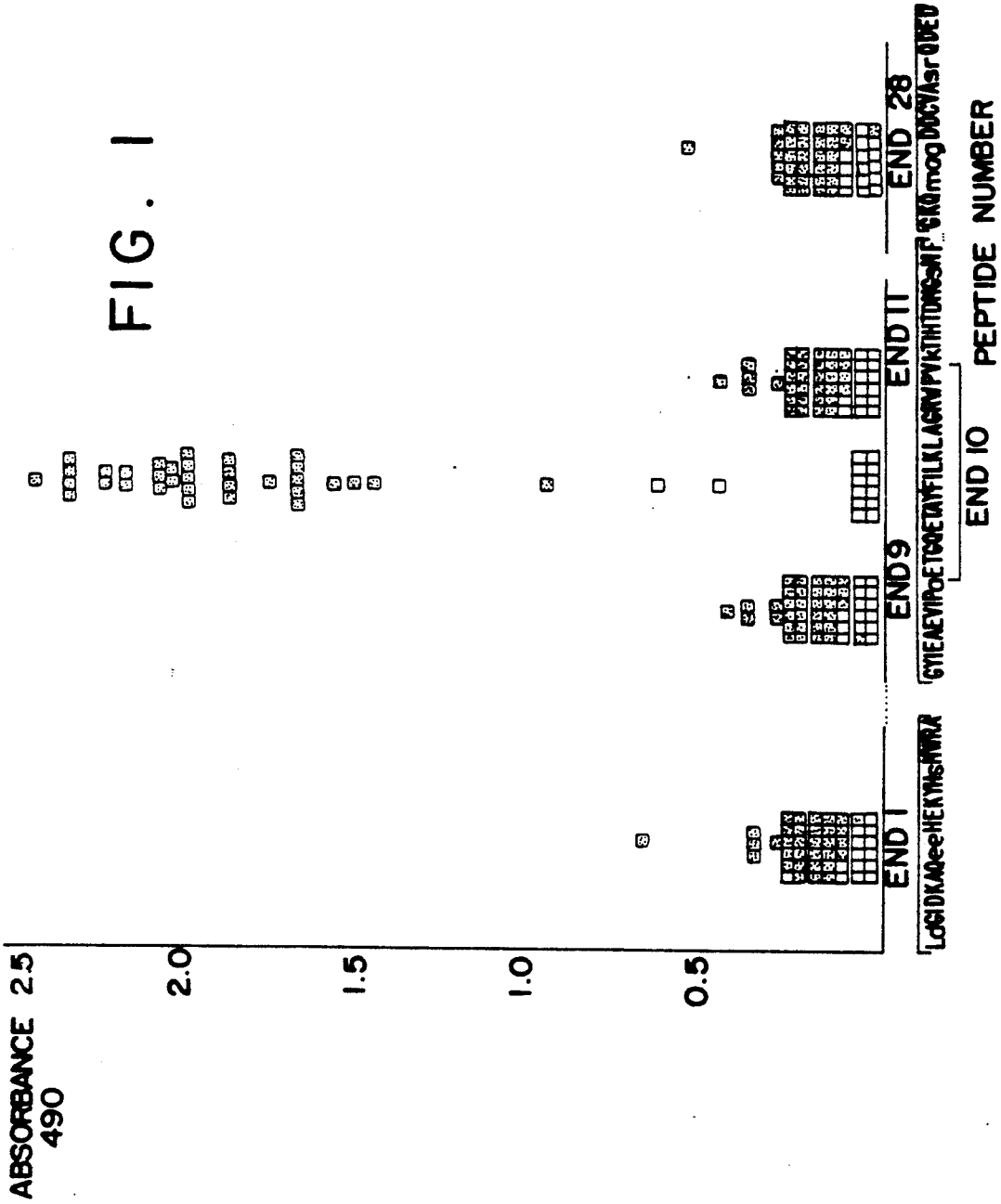

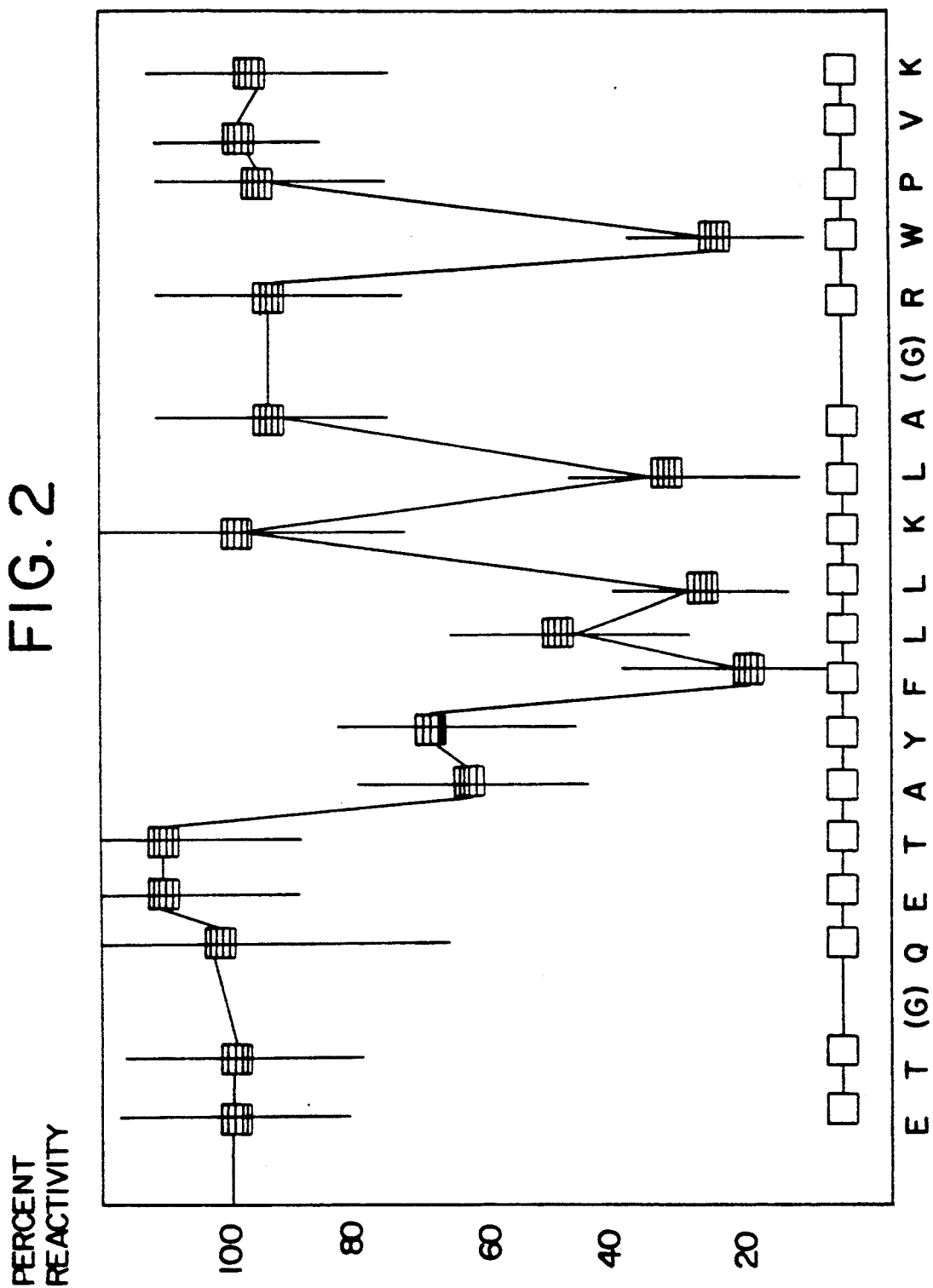

POLYPEPTIDES DERIVED FROM THE HUMAN IMMUNODEFICIENCY VIRUS ENDONUCLEASE PROTEIN

TECHNICAL FIELD

The present invention relates to polypeptides useful in detecting anti-HIV endonuclease antibodies indicative of HIV infection.

BACKGROUND

The identification of antigenic structures encoded by the human immunodeficiency (HIV) genome is relevant for the development of vaccines and serological tests. Several highly reactive antigenic sites have been identified in the env and gag-encoded proteins of HIV-1 and HIV-2 (8-13). Peptides derived from the antigenic sequence located at the $NH_2$ terminal of the transmembrane protein, allow a categorical distinction of antibodies to the two HIV types (12), whereas cross-reactivity between the two serotypes has been found for those regions showing sequence homology (12-14). However, serum reactivity to the gag and env cross-reacting regions is often very low and not all HIV-1 antibody positive sera score positive when tested in serological tests based on the cross-reacting peptides.

One of the features of the life cycle of retroviruses is the insertion of the proviral DNA into host chromosomes. A protein encoded by the 3' end of the pol gene of the virus genome has been shown to possess endonuclease activity (1) which is necessary for DNA integration. Sera from the majority of human immunodeficiency virus (HIV) infected individuals react with the endonuclease protein p31 in serological tests (2-4). It is not known, however, which part of the protein represents the target(s) for antibody response.

BRIEF SUMMARY OF THE INVENTION

The present invention comtemplates a polypeptide of the formula (SEQ ID NO 1):

X—Glu—Thr—Gly—Gln—Glu—Thr—Ala—Tyr—Phe—B
    Leu—Lys—Leu—Ala—Gly—Arg—Trp—Pro—Val—Lys—Z wherein:
 B is Leu or Ile,
 X is a chain of 1 to 20 amino acid residues or an amino-terminal group; and
 Z is a chain of 1 to 20 amino acid residues or a carboxy-terminal group.

Pharmaceutical compositions, preferably in unit does form, of a polypeptide or antibody of this invention are also contemplated, such compositions being useful for detecting anti-HIV endonuclease antibodies.

BRIEF DESCRIPTION OF THE DRAWINGS

In the drawings forming a portion of the specification:

FIG. 1 illustrates the reactivity of sera from HIV-1 infected and non-infected individuals to selected HIV-1 endonuclease peptides. Thirty-three HIV-1 antibody positive sera (filled symbols) and fourteen control sera (open symbols) were analyzed in ELISA with peptides representing the HIV-1 endonuclease protein (6). Amino acid sequences were derived from the HIV-1 consensus sequence and are shown at the bottom of the picture (abscissa). Uppercase letters indicate consensus amino acids, whereas less conserved amino acids are indicated with lowercase letters. Absorbance values at 490 nm are indicated in the ordinate. Three of the sera belonged to infected individuals classified as CDC 1 (7), thirteen to CDCII, seven to CDC III and ten to CDC IV. Becaused reactivity to other regions than the one represented by End 10 was very low, only results of a selected number of peptides is shown in the figure. FIG. 2 illustrates the reactivity of HIV-1 antobidy positive and control sera to an End 10 set of 18 glycine (G) substitution peptides. Filled symbols show mean optical density for 13 antibody positive sera. The corresponding values for four negative sera are shown by open symbols. Vertical bars represent standard deviation values. The mean reactivity to intact peptide End 10 was chosen to represent 100% of activity and reactivity to the substituted peptides is expressed in relation to this. Substitution of a G to amino acids F (position 663) of the HIV-1 pol.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino- or carboxy-terminus of a polypeptide. COOH refers to the free carboxy group present at the carboxy terminus of a polypeptide. The amino-terminal $NH_2$ group and carboxy-terminal COOH group of free polypeptides are typically not set forth in a formula. A hyphen at the amino- or carboxy-terminus of a sequence indicates the presence of a further sequence of amino acid residues or a respective $NH_2$ or COOH terminal group. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus.

Polypeptide: refers to a linear series of amino acid residues connected to one another by peptide bonds between the alpha-amino groups and carboxy groups of contiguous amino acid residues.

Peptide as used herein refers to a linear series of no more than about 50 amino acid residues connected one to the other as in a polypeptide.

Protein: refers to a linear series of greater than 50 amino acid residues connected one to the other as in a peptide.

Synthetic peptide: refers to a chemically produced chain of amino acid residues linked together by peptide bonds that is free of naturally occurring proteins and fragments thereof.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleosides is typically referred to herein as a "nucleotide sequence", and is represented herein by a formula whose left to right orientation is in the conventional direction of 5' terminus to 3' terminus

B. Polypeptides

In one embodiment, the present invention contemplates a polypeptide characterized by the formula (SEQ ID NO 1):

$$X_n\text{—Glu—Thr—Gly—Gln—Glu—Thr—Ala—Tyr—Phe—B} \quad (F1)$$
$$\text{Leu—Lys—Leu—Ala—Gly—Arg—Trp—Pro—Val—Lys—}Z_m.$$

B is either Leu or Ile, preferably Leu. X and Z each represent amino- and carboxy-terminal groups, respectively. The presence or absence of X is indicated by its subscript, n, which is either 0 or 1 such that when n is 0, X is not present and when n is 1 X is present. Similarly, when m is 0, Z is not present and when m is 1, Z is present. Preferably, n=0 and m=1. Preferably, n=1 and m=0. Preferably, n=1 and m=1. X can be an amino-terminal $NH_2$ group. X can also be a chain of 1 to about 20 amino acid residues that is present when n is 1 and is not present when n is 0. Z can be a carboxyterminal COOH group or a carboxy-terminal $NH_2$ group. Z can also be a chain of 1 to about 20 amino acid residues that is present when m is 1 and not present when m is 0.

X can be one of the following amino acid residue sequences (SEQ ID NOs 2-8 correspond to sequences (a)–(g), respectively):

(a) $NH_2$—Gly—Tyr—Ile—Glu—Ala—Glu—Val—Ile—Pro—Ala
(b) $NH_2$—Gly—Tyr—Ile—Glu—Ala—Glu—Val—Ile—Pro
(c) $NH_2$—Gly—Tyr—Ile—Glu—Ala—Glu—Val—Ile
(d) $NH_2$—Gly—Tyr—Ile—Glu—Ala—Glu—Val
(e) $NH_2$—Gly—Tyr—Ile—Glu—Ala—Glu
(f) $NH_2$—Gly—Tyr—Ile—Glu—Ala
(g) $NH_2$—Gly—Tyr—Ile—Glu
(h) $NH_2$—Gly—Tyr—Ile
(i) $NH_2$—Gly—Tyr
(j) $NH_2$—Gly

Z can be one of the following amino acid residue sequences (SEQ ID NOs 9-15 correspond to sequences (a)–(g), respectively):

(a) Thr—Ile—His—Thr—Asp—Asn—Gly—Ser—Asn—Phe—COOH
(b) Thr—Ile—His—Thr—Asp—Asn—Gly—Ser—Asn—COOH
(c) Thr—Ile—His—Thr—Asp—Asn—Gly—Ser—COOH
(d) Thr—Ile—His—Thr—Asp—Asn—Gly—COOH
(e) Thr—Ile—His—Thr—Asp—Asn—COOH
(f) Thr—Ile—His—Thr—Asp—COOH
(g) Thr—Ile—His—Thr—COOH
(h) Thr—Ile—His—COOH
(i) Thr—Ile—COOH
(j) Thr—COOH

In another embodiment, a polypeptide of this invention has the formula (SEQ ID NO 16):

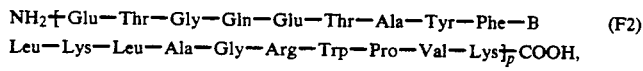

wherein B is either Ile or Leu, preferable Leu. The value of p is an integer such that the homoblock polymer is soluble in aqueous 0.15 M sodium chloride. Preferably the value of p is 2 to about 6.

A preferred polypeptide has less than about 30 amino acid residues and contains an immunologically active sequence, exhibiting cell attachment activity, of the sequence represented by the formula (SEQ ID NO 17):

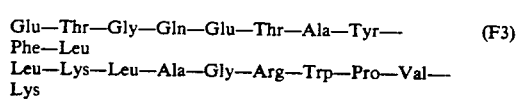

More preferred is a polypeptide according to formula (SEQ ID NO 18):

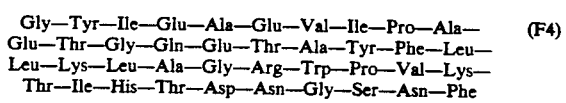

Each of the polypeptides of this invention are characterized as having the ability to immunologically mimic the HIV endonuclease (p31).

In preferred embodiments, a subject polypeptide is operatively linked to a solid matrix, such as agarose, polycarbonate, polystyrene, polypropylene, nitrocellulose, polyester, glass, synthetic resin, latex, long chain polysaccharide and the like. Preferably, the subject polypeptides are operatively linked to a solid matrix forming a diagnostic device, such as a microliter plate well, and the like.

A subject polypeptide includes any analog, fragment or chemical derivative of a polypeptide whose amino acid residue sequence is shown herein so long as the polypeptide is capable of immunologically binding to antibodies induced by the HIV endonuclease protein p31. Therefore, a present polypeptide can be subject to various changes, substitutions, insertions, and deletions where such changes provide for certain advantages in their use.

The term "analog" refers to any polypeptide having an amino acid residue sequence substantially identical to a sequence specifically shown herein in which one or more residues have been conservatively substituted with a functionally similar residue. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatives by reaction of a functional side group. Such derivatized molecules include for example, those molecules ·in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters of hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite binding activity is maintained.

The term "fragment" refers to any subject polypeptide having an amino acid residue sequence shorter than that of a polypeptide whose amino acid residue sequence is shown herein.

A subject polypeptide can be prepared using the solid-phase synthetic technique initially described by Merrifield, in *J. Am. Chem. Soc.*, 85:2149-2154 (1963). Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Piece Chemical Company, Rockford, Ill., 3d Ed., Neurath, H. et al., Eds., p. 104-237, Academic Press, New York, N.Y. (1976). Appropriate protective groups for use in such synthesis will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

A polypeptide of his invention can have a C-terminal amide group. C-terminal amides, such as peptides according to formula p2, can normally be synthesized at a slightly higher purity than the cparable C-terminal acid, for the reasons described below. Normally, peptides with a C-terminal acid are cleaved in 92.5% HF/7.5% anisole for one hour. This involves an "SN1" type reaction where anisole is used as a scavenger. During this type of reaction, the side chain protecting grups which are removed yield free benzyl-type carbocations which can react with other regions of the peptide (i.e., Met, Trp, and Cys residues) instead of the anisole scavenger. These reactions can be avoided if an "SN2" type reaction is used for cleavage. This is done using a modification of Tam's "low/high cleavage" procedure (*Int. J. Pept. Prot. Res.*, 21:57-65, 1983). Using benzhydrylamine resins (which yield C-terminal amides), this reaction cleaves the side chain protecting groups via a milder "SN2" type reaction which involves the unimolecular transfver of the protecting grups frm the peptide to the scavenger (bypassing the reactive carbocation intermediate) while leaving the peptide linked to the resin. (This method of cleavage can not be used for the much more labile resins used in the production of C-terminal acid.) The scavenger byproducts are then rinsed away and the peptide is cleaved from the resin using the standard "SN1" procedure. This usually results in at least a five percent increase in purity for most peptides and is sometimes the difference between success and failure for longer peptides or peptides containing "difficult" residues.

The polypeptides of the present invention generally contain a HIV endonuclease-derived segment of at least 15 amino acid residues and up to fifty amino acid residues, preferably 20-35 amino acid residues. The polypeptides can be linked to an additional sequence of amino acids at either or both the N-terminus and C-terminus, wherein the additional sequences are from 1-100 amino acids in length. Such additional amino acid sequences, or linker sequences, are heterologous to the endonuclease amino acid residue sequence and can be conveniently affixed to a detectable label, solid matrix, or carrier. Labels, solid matrices and carriers that can be used with peptides of the present invention are described below. Typical amino acid residues used for linking are tyrosine, cysteine, lysine, glutamic acid and aspartic acid, and the like. Preferred linking residues are carboxy-terminal Cys and Lys, and amino-terminal Tyr.

Any polypeptide of the present invention, including a chimeric polypeptide as described hereinbelow, may be used in the form of a pharmaceutically acceptable salt. Suitable acids which are capable of forming salts with the polypeptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di and tri-alkyl and aryl amines (e.g. triethylamine, diisopropyl amine, methyl amine, dimethyl amine and the like) and optionally substituted ethanolamines (e.g. ethanolamine, diethanolamine and the like).

The present invention further includes a composition that includes a subject polypeptide in combination with one or more of a pH buffering agent, wetting agent, anti-oxidant, reducing agent, aqueous medium, and the like, such composition being formulated as an aqueous solution for a use as described herein or as a dry composition, such as a powder, that can be reconstituted to form an aqueous solution.

C. Chimeric Polypeptides

A chimeric polypeptide of this invention is defined by the presence of at least one peptide segment defined by the formula (SEQ ID NO 16):

Glu—Thr—Gly—Gln—Glu—Thr—Ala—Tyr—Phe—B
Leu—Lys—Leu—Ala—Gly—Arg—Trp—Pro—Val—Lys, wherein B is either Ile or Leu, preferably Leu, operatively linked via a peptide bond to a peptide segment heterologous to HIV endonuclease.

The HIV endonuclease-derived segments of a subject chimeric polypeptide can be either contiguous or adjacent to each other within the polypeptide chain. Where they are adjacent, the segments are separated by amino acid residues forming a spacer segment typically comprised of from about 5 conveniently up to about 50 residues, preferably about 15 to about 30 residues. A subject chimeric polypeptide can contain a plurality of the same endonuclease segment. Where three or more of the endonuclease segments are adjacent within a subject chimeric polypeptide, the spacer segments can be the same or different.

A subject chimeric polypeptide can further contain a head and/or tail segment of 1 conveniently up to about 50, such as about 5 or out 10, typically about 15 or about 30, at its amino- or carboxy terminus, respectively, where such a segment is advantageous in the polypeptide's making or use. For instance, a tail segment can provide a means for linking the subject chimeric polypeptide to a solid matrix, where as a leader segment can advantageously be used to facilitate secretion of the polypeptide during its expression in cells.

D. DNA and Recombinant DNA Molecules

In living organisms, the amino acid residue sequence of a protein or polypeptide is directly related via the genetic code to the deoxyribonucleic acid (DNA) sequence of the gene that codes for the protein. Thus, a gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

The present invention contemplates a deoxyribonucleic acid (DNA) molecule or segment that defines a gene coding for, i.e., capable of expressing, a subject polypeptide or a subject chimeric polypeptide. A preferred DNA segment has a nucleotide base sequence corresponding to the sequence represented by the formula (SEQ ID NO 19): (F5) GAA ACA GGG CAG GAA ACA GCA TAT TTT CTT TTA AAA TTT GCA GGA AGA TGG CCA GTA AAA.

DNA molecules that encode the subject polypeptides can easily be synthesized by chemical techniques, for example, the phosphotriester method of Matteucci et al., *J. Am. Chem. Soc.*. 103:3185 (1981). Of course, by chemically synthesizing the coding sequence, any desired modifications can be made simply by substituting the appropriate bases for those encoding the native amino acid residue sequence. However, DNA molecules including base sequences identical to all or a portion of that shown above is preferred.

A DNA molecule that includes a DNA sequence encoding a subject polypeptide can be prepared by operatively linking (ligating) appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA molecules.

The present invention further contemplates a recombinant DNA molecule comprising a vector operatively linked, for replication and/or expression, to a subject DNA molecule, i.e., a DNA molecule defining a gene coding for a subject polypeptide or a subject chimeric polypeptide.

As used herein, the term "vector" refers to a DNA molecule capable of autonomous replication in a cell and to which another DNA segment can be operatively linked so as to bring about replication of the attached segment. Vectors capable of directing the expression of a gene delivered by a subject DNA segment are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the subject chimeric polypeptide gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the subject chimeric polypeptide gene in a bacterial host cell, such as E. coli. transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al , *J. Mol. Apol. Genet.,* 1:327-341 (1982).

The use of retroviral expression vectors to form the rDNA of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge, et al., *Mol. Cell. Biol.,* 4:1730-37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase of E. coli DNA polymerase I, enzymes that remove protruding, 3', single-stranded termini with their 3'-5' exonucleotytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophase T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

The present invention also relates to a host cell transformed with a recombinant DNA molecule of the present invention preferably an rDNA capable of expressing a subject chimeric polypeptide. The host cell can be either procaryotic or eucaryotic. Bacterial cells are preferred procaryotic host cells and typically are a strain of E. coli such as, for example, the E. coli strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658. Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.*, 4:1730-37 (1984); Graham et al., *Virol.*, 52:456 (1973); and Wigler et al., *Proc. Natl. Acad Sci. USA*, 76:1373-76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98-503 (1975) or Berent et al., *Biotech.*, 3:208 (1985).

In addition to directly assaying for the presence of rDNA, successful transformation can be confirmed by well known immunological methods when the rDNA is capable of directing the expression of a subject chimeric polypeptide. For example, cells successfully transformed with an expression vector produce proteins displaying HIV endonuclease polypeptide antigenicity. Samples of cells suspected of being transformed are harvested and assayed for the presence of HIV endonuclease antigenicity using antipolypeptide antibodies specific for that peptide segment.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying immunologic cross reactivity with HIV endonuclease.

Nutrient media useful for culturing transformed host cells are well known in the art and can be obtained from several commercial sources. In embodiments wherein the host cell is mammalian, a "serum-free" medium is preferably used.

E. Inocula

In another embodiment, a polypeptide of this invention, preferably a peptide corresponding to formula F1 is used in a pharmaceutically acceptable aqueous diluent composition to form an inoculum that, when administered in an effective amount, is capable of inducing antibodies that immunoreact with HIV endonuclease.

The word "inoculum" in its various grammatical forms is used herein to describe a composition containing a polypeptide of this invention as an active ingredient used for the preparation of antibodies against an Integrin beta subunit.

When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

As already noted, one or more additional amino acid residues can be added to the amino- or carboxy-termini of the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318-326 (1983) and the like, or the use of carbodimide technology as in the use of a water-soluble carbodimide to form amide links to the carrier. For a review of protein conjugation or coupling through activated functional groups, see Aurameas, et al., *Scand. J. Immunol.*, Vol. 8, Suppl. 7:7-23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide or protein per unit dose depends, among other things, on the species of animal inoculated, the body weight of the animal and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent or vehicle such as water, saline or phosphate-buffered saline to form an aqueous composition. Such diluents are well known in the art and are discussed, for example, in *Remington's Pharmaceutical Sciences*, 16th Ed., Mack Publishing Company, Easton, Pa. (1980) at pages 1465-1467.

Inocula can also include an adjuvant as part of the diluent. Adjuvants such as complete Freund's adjuvant (CFA), incomplete Freund's adjuvant (IFA) and alum are materials well known in the art, and are available commercially from several sources.

F. Polyclonal and Monoclonal Anti-peptide Antibodies

An antibody of the present invention, whether polyclonal or monoclonal, immunorreacts with HIV endonuclease and a peptide according to formula F1. The antibody does not immunoreact with a peptide represented by the formula: F4.

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

An "antibody combining site" is that structural portion of an antibody molecule comprised of a heavy and light chain variable and hypervariable regions that specifically binds (immunoreacts with) antigen. The term "immunoreact" in its various forms means binding between an antigenic determinant-containing molecule and a molecule containing an antibody combining site such as a whole antibody molecule or a portion thereof.

"Antigenic determinant" refers to the actual structural portion of the antigen that immunologically bound by an antibody combining site. The terms is also used interchangeably with "epitope".

1. Polyclonal Antibodies

A polyclonal antibody of the present invention immunoreacts with a subject polypeptide, preferably a polypeptide corresponding in amino acid residue sequence to the formula F1. A subject polyclonal antibody is further characterized as not substantially immunoreacting with a polypeptide having an amino acid residue sequence of the formula: F4.

A preferred polyclonal antibody is characterized as having the ability to immunoreact with HIV endonuclease.

A polyclonal antibody of the present invention is typically produced by immunizing a mammal with an inoculum of the present invention, preferably an inoculum containing a peptide corresponding to a Formula I and thereby induce in the mammal antibody molecules having the appropriate polypeptide immunospecificity. The antibody molecules are then collected from the mammal and isolated to the extent desired by well known techniques such as, for example, by immunoaffinity chromatography using the immunizing polypeptide in the solid phase. The polyclonal antibody so produced can be used in, inter alia, the diagnostic methods and systems of the present invention to identify HIV infection.

2. Monoclonal Antibodies

A monoclonal antibody of the present invention is characterized as immunoreacting with an epitope formed by the amino acid residue sequence represented by formula F1. Preferably, a subject monoclonal antibody is further characterized as not immunoreacting with a polypeptide corresponding to the amino acid residue sequence represented by formula F4.

A preferred monoclonal antibody is also characterized as having the ability to immunoreact with HIV endonuclease The phrase "monoclonal antibody" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature* 256:495-497 (1975), which description is incorporated by reference.

3. Methods for Producing A Monoclonal Antibody

The present invention contemplates a method of forming a monoclonal antibody that immunoreacts with a polypeptide of formula F1, but does not immunoreact with a peptide of the formula F4. The method comprises the steps of:

(a) Immunizing an animal with a subject polypeptide, preferably a peptide according to formula F1. This is typically accomplished by administering an immunologically effective amount i.e., an amount sufficient to produce an immune response, of the immunogen to an immunologically competent mammal. Preferably, the mammal is a rodent such as a rabbit, rat or mouse. The mammal is then maintained for a time period sufficient for the mammal to produce cells secreting antibody molecules that immunoreact with the immunogen.

(b) A suspension of antibody-producing cells removed from the immunized mammal is then prepared. This is typically accomplished by removing the spleen of the mammal and mechanically separating the individual spleen cells is a physiologically tolerable medium using methods well known in the art.

(c) The suspended antibody producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/O-Ag14 and the like.

In preferred embodiments, treatment with the transforming agent results in the production of a hybridoma by fusing the suspended spleen cells with mouse myeloma cells from a suitable cell line by the use of a suitable fusion promoter. The preferred ratio is about 5 spleen cells per myeloma cell. A total volume of about $10^8$ splenocytes.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecule weight from about 1000 to about 4000 (commercially available as PEG 1000, etc.), other fusion promoters known in the art maybe employed.

(d) The transformed cells are then cloned, preferably to monoclonality. The cloning is preferably performed in a tissue culture medium that will not support non-transformed cells. When the transformed cells are hybridomas, this is typically performed by diluting and culturing in separate containers, the mixture of unfused spleen cells, unfused myeloma cells, and fused cells (hybridomas) in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1-4) in each separate container (e.g., each well of a microtiter plate). The medium is one (e.g., HAT medium) which will not support the drug-resistant (e.g., 8-azaguanine resistant) unfused myeloma cell line.

(e) The tissue culture medium of the cloned transformants is evaluated for the presence of secreted antibody molecules that immunoreact with HIV endonuclease polypeptide according to formula F1. Peptide positive transformants are preferably further screened to identify those that do not react with the peptide F4.

(f) Once a desired transformant has been identified in step (e), it is selected and grown in a suitable tissue culture medium for a suitable length of time, followed by recovery of the desired antibody from the culture supernatant. The suitable medium and suitable length of culturing time are known or are readily determined.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5–20 mg/ml) in the bloodstream and peritoneal exudate (ascites) of the host mouse.

Media useful for the preparation of these compositions are both well known in the art and commercially available and include synthetic culture media, inbred mice and the like. An exemplary synthetic medium is Dulbecco's minimal essential medium [DMEM; Dulbecco et al., *Virol.* 8:396 (1959)] supplemented with 4.5 gm/1 glucose, 20 mm glutamine, and 20% fetal calf serum. An exemplary inbred mouse strain is the Balb/c.

A monoclonal antibody of the present invention can also be further purified by well known immunoaffinity chromatography methods by using in the solid phase a subject polypeptide with which the antibody immunoreacts.

A monoclonal antibody produced by the above method can be used, for example, in diagnostic and therapeutic modalities wherein formation of a HIV endonuclease-containing immunoreaction product is desired.

G. Hybridomas and Methods of Preparation

Hybridomas of the present invention are those which are characterized as having the capacity to produce a subject monoclonal antibody.

Methods for producing hybridomas producing (secreting) antibody molecules having a desired immunospecificity, i.e., having the ability to immunoreact with a particular protein, an identifiable epitope on a particular protein and/or a polypeptide, are well known in the art. Particularly applicable is the hybridoma technology described by Niman et al., *Proc. Natl. Acad. Sci. USA.* 80:4949–4953 (1983), and by Galfre et al., *Meth. Enzymol.,* 73.3–46 (1981), which descriptions are incorporated herein by reference.

H. Assay Methods

Those skilled in the art will understand that there are numerous heterogeneous and homogeneous methods, immunoassay either competitive or non-competitive, that may be utilized herein. Exemplary, useful solid phase assays include enzyme multiplied immunoassay techniques (EMIT) and fluorescence immune assays (FIA), in addition to the specifically discussed ELISA of Example 2. However, any method that results in a signal imparted by the reaction of antibodies with a polypeptide of this invention is contemplated. Each of those assay methods can employ single or double antibody techniques in which an indicating means is utilized to signal the immunoreaction, and thereby the binding of an antibody that is to be assayed with a polypeptide of this invention. Exemplary techniques can be found explained in Maggio, *Enzyme Immunoassay,* CRC Press, Cleveland, Ohio (1981); and in Goldman, *Fluorescent Antibody Methods,* Academic Press, New York, N.Y. (1980).

A vascular fluid sample is utilized in this assay method. Preferably, the body fluid sample is provided as a known amount of blood or a blood derived product such as serum or plasma, although urine, saliva, semen, vaginal secretion or cerebral-spinal fluid (CSF) can also be used.

One contemplated assay method determines the presence, and preferably the amount of anti-HIV endonuclease antibodies in a vascular fluid sample. This method includes the following steps.

(a) A vascular fluid sample is admixed with a subject polypeptide to form an immunoreaction admixture. The polypeptide preferably is operatively linked to a solid support such that the immunoreaction admixture has both a liquid phase and a solid phase.

(b) The immunoreaction admixture is maintained under biological assay conditions for a time period, typically predetermined, sufficient to form a polypeptide-containing immunoreaction product in the solid phase. In heterogeneous assay formats, the reactants are usually separated after the maintenance period, typically by washing and retaining the solid-phase.

Biological assay conditions are those conditions that are able to sustain the biological activity of the immunochemical reagents of this invention and the antigen sought to be assayed. Those conditions include a temperature range of about 4° C. to about 45° C., a pH value range of about 5 to about 9 and an ionic strength varying from that of distilled water to that of about one molar sodium chloride. Methods for optimizing such conditions are well known in the art.

(c) The presence, and preferably the amount of immunoreaction product formed in step (b) and thereby the presence or amount of anti-HIV endonuclease antibodies in the vascular fluid sample is then determined.

In a preferred embodiment of the above method the amount of immunoreaction product is determined according to step (c) by (i) admixing a labeled specific binding agent capable of binding the polypeptide-containing immunoreaction product to form a labeling reaction admixture, (ii) maintaining the labeling reaction admixture under biological assay conditions for a time period sufficient for the labeled specific binding agent to bind the polypeptide-containing immunoreaction product to form a labeled complex, and (iii) detecting the presence or amount of any labeled complex formed, and thereby detecting the presence or amount of anti-HIV endonuclease antibody-containing immunoreaction product.

In a particularly preferred embodiment, the labeled specific binding agent is labelled anti-IgG.

In another embodiment, the vascular fluid sample is immunoreacted with a subject polypeptide in labeled and unlabeled forms. Typically, the unlabeled polypeptide is attached to a solid-matrix. One arm of the anti-HIV endonuclease antibody will bind the solid-phase polypeptide and another arm of the antibody will bind the labeled polypeptide, thereby forming a solid-phase labeled immunoreaction product. Immunoreactions with the labeled and unlabeled polypeptide can be performed substantially concurrently, i.e., in the same admixture, or serially.

In another embodiment, a subject polypeptide is simultaneously immunoreacted with an anti-polypeptide antibody of this invention and the vascular fluid sample. Preferably, the polypeptide is affixed to the solid support and the anti-polypeptide antibody is labeled. Alternatively, the anti-polypeptide antibody is affixed to the solid-support and the polypeptide is labeled. In either case, a labeled solid-phase immunoreaction product is formed that is indicative of the presence and/or amount of anti-HIV endonuclease antibodies.

Preferably, non-specific protein binding sites on the surface of the solid phase support are blocked. Thus, the solid phase-bound polypeptide is bound as by adsorption or other well known means of affixation to the solid matrix. Thereafter, an aqueous solution of a protein free from interference with the assay such as bovine, horse or other serum albumin that also is free from contamination with HIV endonuclease is admixed with the solid phase to adsorb the admixed protein onto the surface of the polypeptide-containing solid support at protein binding sites on the surface that are not occupied by the monoclonal antibody molecules.

A typical aqueous protein solution contains about 3 to about 10 weight percent bovine serum albumin in PBS at a pH value of 7.1-7.5. The aqueous protein solution-solid support admixture is typically maintained for a time period of at least one hour at 37° C., and the resulting solid phase is thereafter rinsed free of unbound protein.

The vascular fluid sample can be plasma or serum, as already noted. The sample is preferably diluted at about 1:10 to about 1:5000, and more preferably at about 1:10.

I. Diagnostic Systems

The present invention also contemplates a diagnostic system, typically in kit form, that can be utilized in carrying out the before-described assay methods. The system includes, in an amount sufficient for at least one assay, a subject polypeptide as a separately packaged immunochemical reagent. Instructions for use of the packaged reagent are also typically included.

In one embodiment, a diagnostic system in kit form includes a solid support comprising a solid matrix such as a microtiter plate having a polypeptide of this invention affixed thereto (operatively linked to the solid matrix) in an amount sufficient to carry out at least one assay.

In preferred embodiments, the above diagnostic system further includes, as a separately packaged reagent, a second antibody, a reveal antibody, that contains antibody molecules that immunoreact with human IgG. The system can further include, as a separately packaged reagent, an anti-polypeptide antibody of this invention for use in a competition ELISA format.

Preferably, when the label is an enzyme, a diagnostic system further includes one or more of the following: (i) a supply of hydrogen peroxide of known concentration; (ii) a visualizing oxidative dye precursor such as OPD; (iii) a solution of a stopping agent such as 4 N sulfuric acid to quench the color-forming reaction; (iv) one or more buffers in dry or liquid form for use in the assay; and (v) materials for preparing standard reference curves.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are particularly applicable. See, for example, Aurameas, et al., *Scand. J. Immunol.*, Vol. 8 Suppl. 7:7-23 (1978), Rodwell et al., *Biotech.*, 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of apo E in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present.in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

A reagent is typically affixed to a solid matrix by adsorption from an aqueous medium although other modes of affixation applicable to proteins and polypeptides well known to those skilled in the art, can be used.

Thus, in preferred embodiments, a polypeptide, or anti-polypeptide antibody molecule, of the present invention can be affixed in a solid matrix to form a solid support that comprises a package in the subject diagnostic system.

Useful solid matrices are also well known in the art for preparing a solid support containing a reagent affixed thereto. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

EXAMPLES

The following examples illustrate but do not limit the present invention.

1. Peptide Synthesis

To determine the occurrence and location of antigenic sites in the HIV-1 endonuclease protein, twenty-eight linear peptides covering the complete endonuclease sequence were prepared. Those peptides were studied their reactivity in ELISA with human sera from individuals with proven HIV-1 infection. The sequences were derived from the HIV-1 pol consensus sequence (6) and each peptide consisted of 20 amino acid residues with overlapping sequences of 10 residues. Peptide End 1, representing the amino terminus part of the protein, starts with a leucine at position 574 of the HIV-1 consensus pol sequence. Peptide End 28, the last of the series, covers the COOH-terminal part of the protein and ends with an aspartic acid residue at position 809.

The peptides used in the serologic assays were synthesized according to Houghten et al., *Proc. Natl. Acad. Sci. USA.* (1985) 82:5131-5135, and cleaved for the solid phase by the low-high hydrogen flouride procedure of Tam et al., *J. Am. Chem. Soc.,* (1983) 105:6442-6455 in a multivessel apparatus. The peptides were found to be 80-85% homogeneous by HPLC and were therefore used without further purification.

2. Serologic Assays

The peptide ELISA was performed as follows. Microtiter plate wells (Linbro, Flow, Scotland) were coated with peptide (1 µg/well) resuspended in 0.01 M carbonate buffer at room temperature overnight. Thereafter, the plates wells were blocked with 5% bovine serum albumin. 100 µl of reagents were used per well. Five washings (0.9% NaCl and 0.005% Tween 20 in distilled water) were performed between the different steps of the ELISA procedure. Positive sera and controls were diluted 1/100 and incubated in the plates for one hour at 37° C. Peroxidase conjugated immunoglobulins to human IgG y-chains (Dakopatts; Denmark) diluted 1/2000 were added (1 hour, 37° C.). 1,2 phenylene diaminedihydrochloride was used as substrate. The reaction was allowed to continue for ten minutes and then stopped with 3 M $H_2SO_4$. Plates were read at 490 nm in a Titertek spectrophotometer and readings were considered positive when they showed values above the mean optic density of negative human sera plus three standard deviations (S.D.). The mean optic density plus three times S.D. for peptide End 10 was 0.8.

Each peptide was used separately in the ELISA system with HIV-1 infected and negative control sera. None of the 14 antibody-negative control sera reacted with the peptides. All the 33 HIV-1 antibody positive sera, selected from different clinical stages of HIV infection (7), reacted strongly with one of the 28 peptides, End 10 (FIG. 1). Reactivity to the infected sera was still observed at very high dilutions (1:10000). The amino-acid sequence of End 10 is (SEQ ID NO 16) ETG-QETAYFLLKLAGRWPVK. Reactivity to the other parts of the protein did not distinguish reactions of sera obtained from infected or from HIV-1 antibody negative individuals. Consequently, only ELISA results from a few selected peptides are shown in FIG. 1. The amino-acid sequence representing peptide End 10 is located in the central part of the endonuclease protein (starting at position 655) and is highly conserved among different HIV-1 isolates (Table 1).

TABLE 1

Comparison of different HIV-1 and HIV-2 isolates to the HIV-1 consensus sequence representing peptide End 10.

| Strain | Sequence | |
|---|---|---|
| | * * ** * **** *** | |
| HIV-1 consensus | ETGQETAYF?LKLAGRWPVK | (SEQ ID NO 16) |
| HIV-1 BRV | L | (SEQ ID NO 17) |
| HXB2 | L | (SEQ ID NO 17) |
| MN | L | (SEQ ID NO 17) |

TABLE 1-continued

Comparison of different HIV-1 and HIV-2 isolates to the HIV-1 consensus sequence representing peptide End 10.

| Strain | Sequence | |
|---|---|---|
| OYI | I | (SEQ ID NO 20) |
| SF2 | L | (SEQ ID NO 17) |
| HAN | L | (SEQ ID NO 17) |
| RF | I | (SEQ ID NO 20) |
| ELI | L | (SEQ ID NO 17) |
| Z2 | I | (SEQ ID NO 20) |
| NDK | L | (SEQ ID NO 17) |
| MAL | I | (SEQ ID NO 20) |
| HIV-2 consensus | ? RQ L L S IT | (SEQ ID NO 21) |
| HIV-2 ROD | S | (SEQ ID NO 22) |
| NIH2 | S | (SEQ ID NO 22) |
| ISY | S | (SEQ ID NO 22) |
| ST | S | (SEQ ID NO 22) |
| BEN | S | (SEQ ID NO 22) |
| D194 | S | (SEQ ID NO 22) |
| GH1 | S | (SEQ ID NO 22) |
| D205 | T | (SEQ ID NO 23) |

1. Sequences were derived from Meyer et al. (6). The sequence representing the End 10 peptide begins at amino acid 655 of the pol HIV-1 consensus. The corresponding sequence starts at position 519 of the HIV-2 consensus sequence. Letters with asterisks above them indicate those amino acids that are conserved in both HIV-1 and HIV-2 sequenced strains. A ? indicates a substitution as indicated by the residue designated below.

The corresponding region in the genome of HIV-2 (Table 1) and simian immunodeficiency virus (SIV) is also very conserved. Comparison of the HIV-1 sequence with HIV-2 isolates shows and overall homology of 55%. Some amino-acid stretches are, however, completely conserved among the different serotypes. Because of this observation, the HIV-1 peptide End 10 was also tested with 30 sera obtained from HIV-2 infected individuals. Strikingly, all HIV-2 sera reacted strongly with the peptide and the intensity of the reactions was comparable to the ones obtained with HIV-1 sera (data not shown).

Our findings that a peptide from the endonuclease region reacts with all of the HIV-1 and Hiv-2 sera may have important diagnostic implications. A serological test based on the End 10 peptide may assure the identification of individuals protein, or part of it, must be presented in an efficient way to immune-recognition.

3. Substitution Studies

The negative results obtained with peptides End 9 and End 11 demonstrated that parts of both of the amino acid residue sequences ETGQETAYFL (SEQ ID NO 25) and (SEQ ID NO 26) LKLAGRWPVK need to be present to allow reaction with HIV antibodies. In order to determine the relative role of amino acids in peptide End 10, a series of peptides with sequential substitution of the different End 10 residues with glycine were prepared and used in the ELISA.

Whenever the substitution gave a 70% or larger decrease in optical density (490 nm) values in comparison with the intact peptide End 10, the substituted residue was considered to be relevant for antibody binding. Thirteen of the HIV-1 antibody positive sera were used in this experiment. The substitution of any of four amino acids in the central part of the peptide, phenylalanine (amino acid position 663 of the HIV-1 pol consensus sequence), leucines (positions 664 and 666) and tryptophan (position 670), yielded critical optical density reductions (FIG. 2). Since each of the four critical amino acids are interspaced by one or more non-critical residues, the results suggest the presence of a discontinous, unique epitope in the endonuclease protein of HIV.

CITED REFERENCES

1. Grandgenett et al., (1978) *Virology.* 89:119–132.
2. Lillehoj et al., (1988) *J. Virol.*, 62:8; 3053–3058.
3. Steimer et al., (1986) *J. Virol.*, 58(1):9–16.
4. Allan et al., (1987) *Blood*, 69(1):331–333.
5. Houghten et al., (1985) *Proc. Natl. Acad. Sci. USA*, 82:5131–5135.
6. Meyers et al., (1990) *Human retroviruses and AIDS* 1990.
7. Center for Disease Control, (1986) *JAMA* July 4, 256(1):20–25.
8. Wang et al., (1986) *Proc. Natl. Acad. Sci. USA*, 83:6159–6163.
9. Palker et al., (1987) *Proc. Natl. Acad. Sci. USA*, 84:2479–2483.
10. Palker et al., (1988) *Proc. Natl. Acad. Sci. USA*, 85:1932–1936.
11. Norrby et al., (1987) Nature, 329:248–250.
12. Norrby et al., *AIDS Res. Human Retoviruses*, (1991)279–28.
13. Broliden et al., *J. Acquired Immune Deficiency Syndrome*, (1991 4:952–958.
14. Goudsmit et al., (1989) *J. AIDS*, 2:297–302.
15. Kyte et al., (1982) J. Mol. Biol., 157:105–132.
16. Chou et al., (1978) *Adv. Enzymol.*, 47:45–148.
17. Kopchick et al., (1981) J. Virol., 37:274–283.
18. Panet et al., (1975) *Proc. Natl. Acad. Sci.*, 72:2535–2539.
19. Panganiban et al., (1984) *Proc. Natl. Acad. Sci. USA*, 81:7885–7889.
20. Donehower et al., (1984) *Proc. Natl. Acad. Sci. USA*, 81:6461–6465.
21. Tam et al., (1983) *J. Am. Chem. Soc.*, 105:6442–6455.
22. Houghten et al., (1986) *Int. J. Pept. Protein Res.*, 27:675–683.

Although the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( v ) FRAGMENT TYPE: internal ( i x ) FEATURE:
( A ) NAME/KEY: Region
( B ) LOCATION: 1
( D ) OTHER INFORMATION: /note="Xaa corresponds to "X"in the specification, and is a chain of 1 to 20 amino acid residues or an amino-terminal group."

( i x ) FEATURE:
( A ) NAME/KEY: Region
( B ) LOCATION: 11
( D ) OTHER INFORMATION: /note="Xaa corresponds to "B"in the specification, and is Leucine or Isoleucine"

( i x ) FEATURE:
( A ) NAME/KEY: Region
( B ) LOCATION: 22
( D ) OTHER INFORMATION: /note="Xaa corresponds to "Z"in the specifiction, and is a chain of 1 to 20 amino acid residues or a carboxy-terminal group."

( x i ) SEQUENCE DESCRIPTION: SEQ ID NO:1:

```
Xaa Glu Thr Gly Gln Glu Thr Ala Tyr Phe Xaa Leu Lys Leu Ala Gly
1               5                   10                  15

Arg Trp Pro Val Lys Xaa
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Region
        ( B ) LOCATION: 1..10
        ( D ) OTHER INFORMATION: /note="An amino terminal group
            representing amino acid residue "Xaa"at position
            # 1, in Sequence I.D. #Microsoft Corp ( x i ) SEQUENCE DESCRIPTION: SEQ ID NO:2:

Gly Tyr Ile Glu Ala Glu Val Ile Pro Ala
1               5                   10

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Region
        ( B ) LOCATION: 1..9
        ( D ) OTHER INFORMATION: /note="An amino terminal group
            representing amino acid residue "Xaa"at position
            # 1, in Sequence I.D. #Microsoft Corp ( x i ) SEQUENCE DESCRIPTION: SEQ ID NO:3:

Gly Tyr Ile Glu Ala Glu Val Ile Pro
1               5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: N-terminal ( i x ) FEATURE:
        ( A ) NAME/KEY: Region
        ( B ) LOCATION: 1..8
        ( D ) OTHER INFORMATION: /note="An amino terminal group
            representing amino acid residue "Xaa"at position
            # 1, in Sequence I.D. #Microsoft Corp ( x i ) SEQUENCE DESCRIPTION: SEQ ID NO:4:

Gly Tyr Ile Glu Ala Glu Val Ile
1               5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear (i i) MOLECULE TYPE: peptide (v) FRAGMENT TYPE: N-terminal (i x) FEATURE:
    (A) NAME/KEY: Region
    (B) LOCATION: 1..7
    (D) OTHER INFORMATION: /note="An amino terminal group representing amino acid residue "Xaa"at position # 1, in Sequence I.D. #Microsoft Corp (x i) SEQUENCE DESCRIPTION: SEQ ID NO:5:

Gly Tyr Ile Glu Ala Glu Val
1                  5

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (v) FRAGMENT TYPE: N-terminal (i x) FEATURE:
    (A) NAME/KEY: Region
    (B) LOCATION: 1..6
    (D) OTHER INFORMATION: /note="An amino terminal group representing amino acid residue "Xaa"at position # 1, in Sequence I.D. #Microsoft Corp (x i) SEQUENCE DESCRIPTION: SEQ ID NO:6:

Gly Tyr Ile Glu Ala Glu
1                  5

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (i i) MOLECULE TYPE: peptide (v) FRAGMENT TYPE: N-terminal (i x) FEATURE:
    (A) NAME/KEY: Region
    (B) LOCATION: 1..5
    (D) OTHER INFORMATION: /note="An amino terminal group representing amino acid residue "Xaa"at position # 1, in Sequence I.D. #Microsoft Corp (x i) SEQUENCE DESCRIPTION: SEQ ID NO:7:

Gly Tyr Ile Glu Ala
1                  5

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (i i) MOLECULE TYPE: peptide (v) FRAGMENT TYPE: N-terminal (i x) FEATURE:
    (A) NAME/KEY: Region
    (B) LOCATION: 1..4
    (D) OTHER INFORMATION: /note="An amino terminal group representing amino acid residue "Xaa"at position # 1, in Sequence I.D. #Microsoft Corp ( x i ) SEQUENCE DESCRIPTION: SEQ ID NO:8:

Gly Tyr Ile Glu
1

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Region
        ( B ) LOCATION: 1..10
        ( D ) OTHER INFORMATION: /note="A carboxy terminal group
            representing amino acid residue "Xaa"at position
            # 22, in Sequence I.D. #Microsoft Corp ( x i ) SEQUENCE DESCRIPTION: SEQ ID NO:9:

Thr Ile His Thr Asp Asn Gly Ser Asn Phe
1           5                   10

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Region
        ( B ) LOCATION: 1..9
        ( D ) OTHER INFORMATION: /note="A carboxy terminal group
            representing amino acid residue "Xaa"at position
            # 22, in Sequence I.D. #Microsoft Corp ( x i ) SEQUENCE DESCRIPTION: SEQ ID NO:10:

Thr Ile His Thr Asp Asn Gly Ser Asn
1           5

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: C-terminal ( i x ) FEATURE:
        ( A ) NAME/KEY: Region
        ( B ) LOCATION: 1..8
        ( D ) OTHER INFORMATION: /note="A carboxy terminal group
            representing amino acid residue "Xaa"at position
            # 22, in Sequence I.D. #Microsoft Corp ( x i ) SEQUENCE DESCRIPTION: SEQ ID NO:11:

Thr Ile His Thr Asp Asn Gly Ser
1           5

( 2 ) INFORMATION FOR SEQ ID NO:12:

( i ) SEQUENCE CHARACTERISTICS:

(A) LENGTH 7 amino acids
(B) TYPE: amino acid
(D) TOPOLOGY: linear (ii) MOLECULE TYPE: peptide (v) FRAGMENT TYPE: C-terminal (ix) FEATURE:
(A) NAME/KEY: Region
(B) LOCATION: 1..7
(D) OTHER INFORMATION: /note="A carboxy terminal group representing amino acid residue "Xaa"at position # 22, in Sequence I.D. #Microsoft Corp (xi) SEQUENCE DESCRIPTION: SEQ ID NO:12:

Thr Ile His Thr Asp Asn Gly
1               5

(2) INFORMATION FOR SEQ ID NO:13:

(i) SEQUENCE CHARACTERISTICS:
(A) LENGTH: 6 amino acids
(B) TYPE: amino acid
(D) TOPOLOGY: linear (ii) MOLECULE TYPE: peptide (v) FRAGMENT TYPE: C-terminal (ix) FEATURE:
(A) NAME/KEY: Region
(B) LOCATION: 1..6
(D) OTHER INFORMATION: /note="A carboxy terminal group representing amino acid residue "Xaa"at position # 22, in Sequence I.D. #Microsoft Corp (xi) SEQUENCE DESCRIPTION: SEQ ID NO:13:

Thr Ile His Thr Asp Asn
1               5

(2) INFORMATION FOR SEQ ID NO:14:

(i) SEQUENCE CHARACTERISTICS:
(A) LENGTH: 5 amino acids
(B) TYPE: amino acid
(D) TOPOLOGY: linear (ii) MOLECULE TYPE: peptide (v) FRAGMENT TYPE: C-terminal (ix) FEATURE:
(A) NAME/KEY: Region
(B) LOCATION: 1..5
(D) OTHER INFORMATION: /note="A carboxy terminal group representing amino acid residue "Xaa"at position # 1, in Sequence I.D. #Microsoft Corp (xi) SEQUENCE DESCRIPTION: SEQ ID NO:14:

Thr Ile His Thr Asp
1               5

(2) INFORMATION FOR SEQ ID NO:15:

(i) SEQUENCE CHARACTERISTICS:
(A) LENGTH: 4 amino acids
(B) TYPE: amino acid
(D) TOPOLOGY: linear (ii) MOLECULE TYPE: peptide (v) FRAGMENT TYPE: C-terminal (ix) FEATURE:
(A) NAME/KEY: Region (B) LOCATION: 1..4
(D) OTHER INFORMATION: /note="A carboxy terminal group
representing amino acid residue "Xaa"at position
22, in Sequence I.D. #Microsoft Corp (x i) SEQUENCE DESCRIPTION: SEQ ID NO:15:

Thr  Ile  His  Thr
1

(2) INFORMATION FOR SEQ ID NO:16:

(i) SEQUENCE CHARACTERISTICS:
        (A) LENGTH: 20 amino acids
        (B) TYPE: amino acid
        (D) TOPOLOGY: linear (i i) MOLECULE TYPE: peptide (v) FRAGMENT TYPE: internal (i x) FEATURE:
        (A) NAME/KEY: Region
        (B) LOCATION: 10
        (D) OTHER INFORMATION: /note="Xaa corresponds to "B"in
the specification, and is either Isoleucine or Leucine, preferabl (i x) FEATURE:
        (A) NAME/KEY: Region
        (B) LOCATION: 1..20
        (D) OTHER INFORMATION: /label=Homoblock
            / note="This sequence is a "homoblock"represented
by the value "p", where the value p is an integer,
preferably from 2 to about 6."

(x i) SEQUENCE DESCRIPTION: SEQ ID NO:16:

Glu  Thr  Gly  Gln  Glu  Thr  Ala  Tyr  Phe  Xaa  Leu  Lys  Leu  Ala  Gly  Arg
1                  5                            10                       15

Trp  Pro  Val  Lys
              20

(2) INFORMATION FOR SEQ ID NO:17:

(i) SEQUENCE CHARACTERISTICS:
        (A) LENGTH: 20 amino acids
        (B) TYPE: amino acid
        (D) TOPOLOGY: linear (i i) MOLECULE TYPE: peptide (v) FRAGMENT TYPE: internal (x i) SEQUENCE DESCRIPTION: SEQ ID NO:17:

Glu  Thr  Gly  Gln  Glu  Thr  Ala  Tyr  Phe  Leu  Leu  Lys  Leu  Ala  Gly  Arg
1                  5                            10                       15

Trp  Pro  Val  Lys
              20

(2) INFORMATION FOR SEQ ID NO:18:

(i) SEQUENCE CHARACTERISTICS:
        (A) LENGTH: 40 amino acids
        (B) TYPE: amino acid
        (D) TOPOLOGY: linear (i i) MOLECULE TYPE: peptide (v) FRAGMENT TYPE: internal (x i) SEQUENCE DESCRIPTION: SEQ ID NO:18:

Gly  Tyr  Ile  Glu  Ala  Glu  Val  Ile  Pro  Ala  Glu  Thr  Gly  Gln  Glu  Thr
1                  5                            10                       15

Ala  Tyr  Phe  Leu  Leu  Lys  Leu  Ala  Gly  Arg  Trp  Pro  Val  Lys  Thr  Ile

```
                20                         25                        30
```

His Thr Asp Asn Gly Ser Asn Phe
            35                    40

( 2 ) INFORMATION FOR SEQ ID NO:19:

( i ) SEQUENCE CHARACTERISTICS:
       ( A ) LENGTH: 60 base pairs
       ( B ) TYPE: nucleic acid
       ( C ) STRANDEDNESS: double
       ( D ) TOPOLOGY: linear ( i i ) MOLECULE TYPE: DNA (genomic)

( i x ) FEATURE:
       ( A ) NAME/KEY: CDS
       ( B ) LOCATION: 1..60

( x i ) SEQUENCE DESCRIPTION: SEQ ID NO:19:

```
GAA  ACA  GGG  CAG  GAA  ACA  GCA  TAT  TTT  CTT  TTA  AAA  TTT  GCA  GGA  AGA         48
Glu  Thr  Gly  Gln  Glu  Thr  Ala  Tyr  Phe  Leu  Leu  Lys  Phe  Ala  Gly  Arg
 1              5                        10                       15

TGG  CCA  GTA  AAA                                                                      60
Trp  Pro  Val  Lys
              20
```

( 2 ) INFORMATION FOR SEQ ID NO:20:

( i ) SEQUENCE CHARACTERISTICS:
       ( A ) LENGTH: 20 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:20:

```
Glu  Thr  Gly  Gln  Glu  Thr  Ala  Tyr  Phe  Ile  Leu  Lys  Leu  Ala  Gly  Arg
 1              5                        10                       15

Trp  Pro  Val  Lys
              20
```

( 2 ) INFORMATION FOR SEQ ID NO:21:

( i ) SEQUENCE CHARACTERISTICS:
       ( A ) LENGTH: 20 amino acids
       ( B ) TYPE: amino acid
       ( D ) TOPOLOGY: linear ( i i ) MOLECULE TYPE: peptide ( v ) FRAGMENT TYPE: internal ( i x ) FEATURE:
       ( A ) NAME/KEY: Region
       ( B ) LOCATION: 2
       ( D ) OTHER INFORMATION: /note="Amino acid "Xaa"at
             position #Microsoft Corp
"in the specificationsponds to the "

( x i ) SEQUENCE DESCRIPTION: SEQ ID NO:21:

```
Glu  Xaa  Gly  Arg  Gln  Thr  Ala  Leu  Phe  Leu  Leu  Lys  Leu  Ala  Ser  Arg
 1              5                        10                       15

Trp  Pro  Ile  Thr
              20
```

( 2 ) INFORMATION FOR SEQ ID NO:22:

( i ) SEQUENCE CHARACTERISTICS:
       ( A ) LENGTH: 20 amino acids (B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:22:

```
Glu Ser Gly Arg Gln Thr Ala Leu Phe Leu Leu Lys Leu Ala Ser Arg
1               5                   10                  15
Trp Pro Ile Thr
            20
```

(2) INFORMATION FOR SEQ ID NO:23:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:23:

```
Glu Thr Gly Arg Gln Thr Ala Leu Phe Leu Leu Lys Leu Ala Ser Arg
1               5                   10                  15
Trp Pro Ile Thr
            20
```

(2) INFORMATION FOR SEQ ID NO:24:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Region
        (B) LOCATION: 1
        (D) OTHER INFORMATION: /note="Wherein "Xaa"at position
        # 1 corresponds to "X"in the specification, and is
a chain of from 1 to 20 amino acid residues
        or an amino-terminal group."

(ix) FEATURE:
        (A) NAME/KEY: Region
        (B) LOCATION: 22
        (D) OTHER INFORMATION: /note="Wherein "Xaa"at position
        # 22 corresponds to "Z"in the specification, and is
a chain of from 1 to 20 amino acid residues
        or a carboxy-terminal group."

(xi) SEQUENCE DESCRIPTION: SEQ ID NO:24:

```
Xaa Glu Thr Gly Gln Glu Thr Ala Tyr Phe Ile Leu Lys Leu Ala Gly
1               5                   10                  15
Arg Trp Pro Val Lys Xaa
                    20
```

(2) INFORMATION FOR SEQ ID NO:25:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (x i) SEQUENCE DESCRIPTION: SEQ ID NO:25:

```
Glu Thr Gly Gln Glu Thr Ala Tyr Phe Leu
1               5                   10
```

(2) INFORMATION FOR SEQ ID NO:26:

(i) SEQUENCE CHARACTERISTICS:
    (A) LENGTH: 10 amino acids
    (B) TYPE: amino acid
    (D) TOPOLOGY: linear (ii) MOLECULE TYPE: peptide (v) FRAGMENT TYPE: internal (x i) SEQUENCE DESCRIPTION: SEQ ID NO:26:

```
Leu Lys Leu Ala Gly Arg Trp Pro Val Lys
1               5                   10
```

What is claimed is:

1. A polypeptide of the formula (SEQ ID NO 1):

X—Glu—Thr—Gly—Gln—Glu—Thr—Ala—Tyr—Phe—Xaa—Leu—Lys—Leu—Ala—Gly—Arg—Trp—Pro—Val—Lys—Z wherein:
  Xaa is Leu or Ile,
  X is a chain of 1 to 10 amino acid residues selected from the group consisting of Gly—Tyr—Ile—Glu—Ala—Glu—Val—Ile—Pro—Ala (SEQ ID NO:2);

Gly—Tyr—Ile—Glu—Ala—Glu—Val—Ile—Pro (SEQ IN NO:3);

Gly—Tyr—Ile—Glu—Ala—Glu—Val—Ile (SEQ ID NO:4);

Gly—Tyr—Ile—Glu—Ala—Glu—Val (SEQ ID NO:5);

Gly—Tyr—Ile—Glu—Ala—Glu (SEQ ID NO:6);

Gly—Tyr—Ile—Glu—Ala (SEQ ID NO:7);

Gly—Tyr—Ile—Glu (SEQ ID NO:8);

Gly—Tyr—Ile;

Gly—Tyr; and

Gly;

or an amino-terminal NH2 group; and
Z is a chain of 1 to 10 amino acid residues selected from the group consisting of Thr—Ile—His—Thr—Asp—Asn—Gly—Ser—Asn—Phe (SEQ ID NO:9);

Thr—Ile—His—Thr—Asp—Asn—Gly—Ser—Asn (SEQ ID NO:10);

Thr—Ile—His—Thr—Asp—Asn—Gly—Ser (SEQ ID NO:11);

Thr—Ile—His—Thr—Asp—Asn—Gly (SEQ ID NO:12);

Thr—Ile—His—Thr—Asp—Asn (SEQ ID NO:13);

Thr—Ile—His—Thr—Asp (SEQ ID NO:14);

Thr—Ile—His—Thr (SEQ ID NO:15);

Thr—Ile—His;

Thr—Ile; and

Thr;

or a carboxy-terminal COOH or CONH2 group.

2. The polypeptide of claim 1 wherein X is represented by the formula:

Gly-Tyr-Ile-Glu-Ala-Glu-Val-Ile-Pro-Ala (SEQ ID NO 3).

3. The polypeptide of claim 1 wherein Z is represented by the formula:

Thr-Ile-His-Thr-Asp-Asn-Gly-Ser-Asn-Phe (SEQ ID NO 9).

4. A polypeptide of the formula (SEQ ID NO 17)

(SEQ ID NO: 17)

Glu—Thr—Gly—Gln—Glu—Thr—Ala—Tyr—Phe—Leu
Leu—Lys—Leu—Ala—Gly—Arg—Trp—Pro—Val—Lys.

5. A polypeptide having the formula (SEQ ID NO 17):

NH2(Glu—Thr—Gly—Gln—Glu—Thr—Ala—Tyr—Phe—Xaa—Leu—Lys—Leu—Ala—Gly—Arg—Trp—Pro—Val—Lys)$_p$ COOH wherein Xaa is Leu or Ile; and p is an integer having a value of 2 to 6.

* * * * *